(12) United States Patent
Hussam et al.

(10) Patent No.: US 10,534,822 B1
(45) Date of Patent: Jan. 14, 2020

(54) SEARCH ENGINE FOR SEARCHING AN INSTRUMENT INDEX

(71) Applicant: Universal Research Solutions, LLC, Columbia, MO (US)

(72) Inventors: Ali Adel Hussam, Columbia, MO (US); Nathan Bleigh, Kansas City, MO (US); Sowjanya Paladugu, Columbia, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 225 days.

(21) Appl. No.: 15/265,254

(22) Filed: Sep. 14, 2016

(51) Int. Cl.
| | |
|---|---|
| *G06F 7/00* | (2006.01) |
| *G06F 17/00* | (2019.01) |
| *G06F 16/9535* | (2019.01) |
| *G16H 50/70* | (2018.01) |
| *G06F 16/248* | (2019.01) |
| *G06F 16/22* | (2019.01) |

(52) U.S. Cl.
CPC ...... *G06F 16/9535* (2019.01); *G06F 16/2228* (2019.01); *G06F 16/2282* (2019.01); *G06F 16/248* (2019.01); *G16H 50/70* (2018.01)

(58) Field of Classification Search
None
See application file for complete search history.

(56) References Cited

U.S. PATENT DOCUMENTS

| | | | |
|---|---|---|---|
| 2011/0004588 A1* | 1/2011 | Leitersdorf | G06F 17/30864 707/711 |
| 2011/0093796 A1* | 4/2011 | Plummer | G06F 19/363 715/753 |
| 2011/0161105 A1* | 6/2011 | Hussam | G06Q 10/10 705/2 |
| 2014/0081665 A1* | 3/2014 | Holmes | G06F 21/32 705/3 |
| 2016/0048643 A1* | 2/2016 | Woods | G06F 19/327 705/3 |

* cited by examiner

*Primary Examiner* — Tuan A Pham
(74) *Attorney, Agent, or Firm* — Fish & Richardson P.C.

(57) ABSTRACT

Methods, systems, apparatus, including computer programs encoded on computer storage mediums, to employ a benchmarking search engine system. In one aspect, a method includes actions of maintaining a medical study instrument index that organizes data based on procedure type, wherein each index entry in the medical study instrument index includes a procedure type. The actions may further include receiving a search query that identifies particular procedure criteria from a user device, accessing the medical study instrument index that is organized based on procedure type, determining a first output that is representative of biometric data that is independent of a procedure specified by the particular procedure criteria, determining a second output that is representative of biometric data that is dependent on a procedure specified by the particular procedure criteria, and generating a page for display on the user device that includes the first output and the second output.

19 Claims, 7 Drawing Sheets

SEARCH ENGINE FOR SEARCHING AN INSTRUMENT INDEX

BACKGROUND

Medical forms are used to collect data and information regarding a patient's symptoms and conditions. One technique for preparing a medical form is to manually edit a pre-existing form (e.g., a form existing in Microsoft Word™ format) with new or customized questions. The form is then sent to review boards for review through a physical or electronic mailing. Additionally, once a form has been finalized, it may be presented to a patient, study participant or other individual (collectively referred to as "patients" herein, without limitation, for purposes of convenience). For example, physicians may present patients with the forms when the patient visits the physician's office. Additionally, hardcopy (i.e., paper) versions of medical forms may be distributed to patients for completion. For patients who have not completed medical forms prior to the patient's examination, the patient may often complete the medical form at the physician's office by filling out a hardcopy of the form.

Frequently, the patient's responses to the questions included in the medical forms are entered into a computerized system by medical personnel. In this case, in order for a physician to review the patient's responses, the physician may access the computerized system and view the answers to the questions, which is often a lengthy process of reviewing individual questions.

SUMMARY

According to one implementation, the subject matter of this specification may be embodied in a method to facilitate a search engine system. The method may include the actions of maintaining, by a search engine, a medical study instrument index that organizes data based on procedure type, wherein each index entry in the medical study instrument index includes a procedure type, receiving, by the search engine, a search query that identifies particular procedure criteria from a user device, in response to receiving, by the search engine, the search query that identifies the particular procedure criteria, accessing, by the search engine, the medical study instrument index that is organized based on procedure type, determining, by the search engine using one or more index entries in the medical study instrument index, a first output that is representative of biometric data that is independent of a procedure specified by the particular procedure criteria identified in the search query, determining, by the search engine using one or more index entries in the medical study instrument index, a second output that is representative of biometric data that is dependent on a procedure specified by the particular procedure criteria identified in the search query, and generating, by the search engine, a page for display on the user device that includes the first output and the second output.

Other versions include corresponding systems, apparatus, and computer programs to perform actions of methods, encoded on computer storage devices.

These and other versions may optionally include one or more of the following features. For instance, in some implementations, maintaining, by a search engine, a medical study instrument index that organizes data based on procedure type, wherein each index entry in the medical study instrument index includes a procedure type may include obtaining one or more populated medical study instruments, for each particular medical study instrument of the one or more obtained medical study instruments: extracting treatment data from one or more fields of the particular medical study instrument, wherein the extracted treatment data includes a procedure type, generating an index entry for the particular medical study instrument that includes the procedure type, and storing the generated index entry in the medical study instrument index.

In some implementations, accessing, by the search engine, the medical study instrument index that is organized based on procedure type may include identifying, by the search engine, a set of index entries that include a procedure type that satisfies the procedure criteria identified in the search query.

In some implementations, the first output that is representative of biometric data that is independent of the procedure specified by the particular procedure criteria identified in the search query may include an average of multiple scores that each indicate the state of an entity prior to the entity receiving the procedure specified by the particular procedure criteria identified in the search query.

In some implementations, the second output that is representative of biometric data that is dependent on a procedure specified by the particular procedure criteria identified in the search query may include an average of multiple scores that each indicate the state of an entity after the entity has received the procedure specified by the particular procedure criteria identified in the search query.

In some implementations, generating, by the search engine, a page for display on the user device that includes the first output and the second output may include generating a bar graph that includes a first bar and a second bar, wherein the first bar provides a graphical representation of a value associated with the first output and the second bar provides a graphical representation of a value associated with the second output.

In some implementations, generating, by the search engine, a page for display on the user device that includes the first output and the second output may include generating a table that includes a first row and a second row, wherein the first row includes a numerical representation of a value associated with the first output and the second row provides numerical representation of a value associated with the second output.

The details of one or more embodiments of the subject matter described in this specification are set forth in the accompanying drawings and the description below. Other features, aspects, and advantages of the subject matter will become apparent from the description, the drawings, and the claims.

WRITTEN DESCRIPTION

In some implementations, a system is disclosed that may be used to generate a medical study instrument index that is organized based on a procedure type. The medical study instrument index improves the functionality of a machine by increasing the efficiency with which data corresponding to multiple different medical study instruments can be accessed. In addition, in some implementations, the medical study instrument index optimizes storage space by eliminating the need to store each respective medical study instrument in their respective entireties. Instead, the medical study instrument index may index a score that was derived from data populated into one or more fields of a corresponding medical study instrument. A user may interact with a search engine which can access the medical study instrument index, and provide information in response to the user's interaction that is related to a healthcare institution or a healthcare provider. Data derived from the search results may be used to evaluate a healthcare institution's performance, a healthcare provider's performance, or both.

Figure 1:
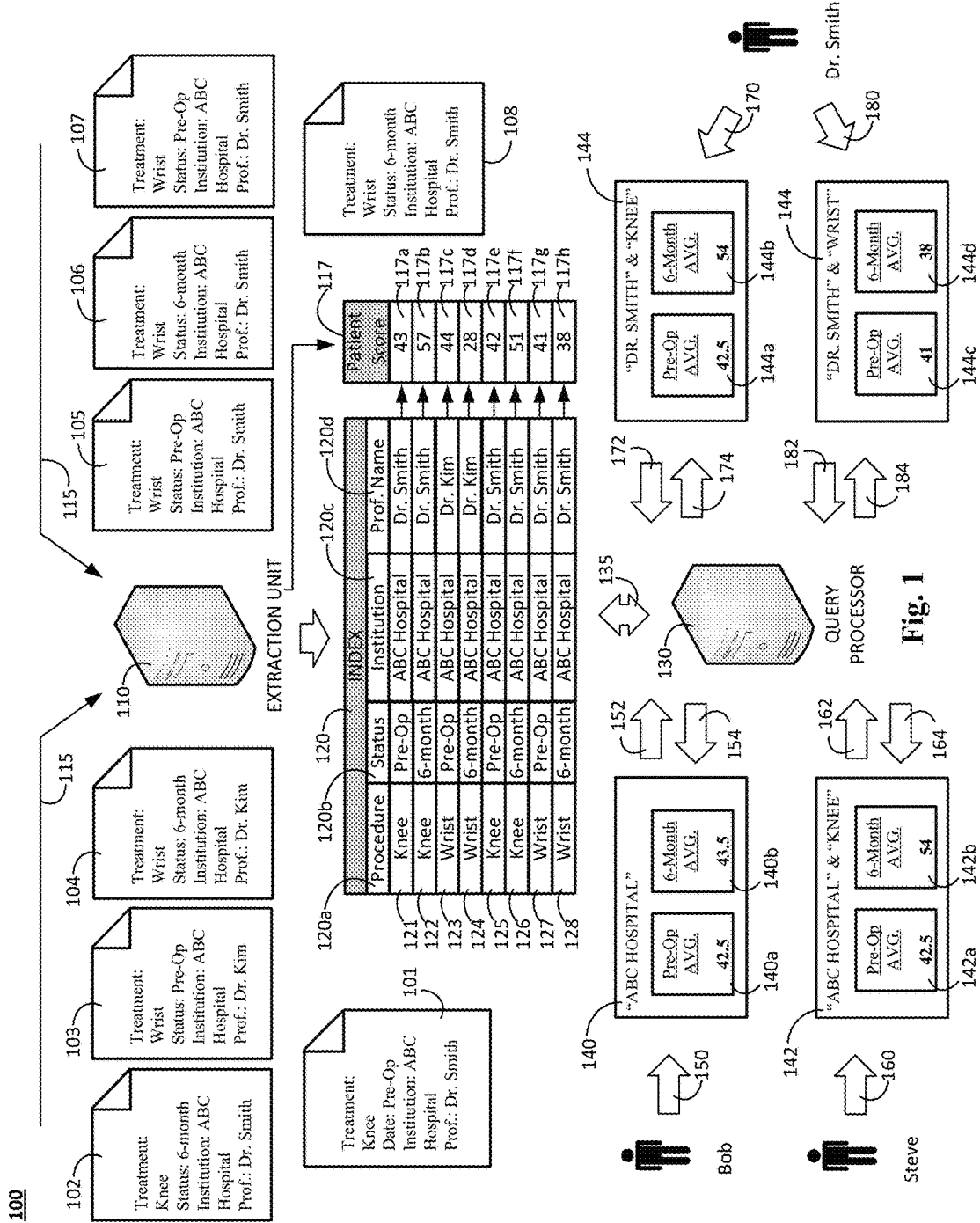
FIG. 1 is an example of a contextual diagram of an example of a search engine system for generating and accessing a medical study instrument index organized by procedure type.

FIG. 1 is an example of a contextual diagram of an example of a search engine system 100 for generating and accessing a medical study instrument index organized by procedure type. A search engine system may include, for example, software components, hardware components, or a combination of both, that facilitate search and retrieval of information. In one implementation, the search engine system 100 may include a data extraction unit 110, a medical study instrument index 120, and a query processor 130.

The data extraction unit 110 is configured to obtain 115 multiple different medical study instruments such as medical study instruments 102, 103, 104, 105, 106, 107, 108. In one implementation, the data extraction unit 110 may be hosted on one or more servers that can communicate with one or more other computers via one or more networks such as, for example, a LAN, a WAN, a cellular network, the Internet, or the like to obtain each respective medical study instrument of the multiple medical study instruments. The respective one or more other computers may include, for example, one or more server computers, one or more user devices, or both, that can communicate with the data extraction unit 110 via the one or more networks. The user devices may be client devices that include, for example, a desktop computer, a laptop computer, a smart phone, a tablet, a smart watch, other wearable device, or the like.

Obtaining 115 the multiple medical study instruments may include the data extraction unit 110, or another server associated with system 100, obtaining one or multiple different medical study instruments from a local database, requesting one or multiple different medical study instruments from one or more other computers via a network, receiving one or multiple different medical study instruments from one or more other computers via a network, or a combination thereof. The network may include, for example, one or more of a LAN, a WAN, a cellular network, the Internet, or the like. In some implementations, the data extraction unit 110, or another server associated with system 100, may be configured to periodically poll one or more sources of medical study instruments for the existence of new, or updated, medical study instruments. Alternatively, or in addition, the data extraction unit 110, or other servers associated with system 100, may transmit reminders to one or more other computers to complete and return a particular medical study instrument to the data extraction unit, or another server associated system 100.

Each medical study instrument may include, for example, a form or questionnaire that is provided to a patient in order to solicit information from the patient regarding one or more facets of the patient's health. Any particular medical study instrument may be generated to solicit information from a patient regarding the patient's respective pre-procedure health (e.g., patient's pre-operation health), post-procedure health (e.g., a patient's health 6 months after an operation), or the like. A medical study instrument soliciting information relating to a patient's pre-procedure health information may be characterized as including patient data that is independent of the procedure. Similarly, medical study instrument soliciting information related to a patient's post-procedure health information may be characterized as including patient data that is dependent, at least in part, on the procedure. The information solicited in any particular medical study instrument may include biometric data and non-biometric data. Biometric data may include any information that describes a characteristic of the patient's body (e.g., the patient experienced pain in the patient's ACL after knee surgery). Biometric data may include data related to physical or mental aspects of the patient's body. Non-biometric data may include any information that is not related to a characteristic of the patient's body (e.g., the professional who performed the procedure is Dr. Smith). The data that a patient inputs into one or more fields of a medical study instrument may be referred to as patient experience data.

The examples of medical instrument forms 102, 103, 104, 105, 106, 107, 108 depicted in FIG. 1 may include one or more fields that have been populated with non-biometric data. The non-biometric data in each respective field may be obtained my providing a question in a medical instrument form that that is associated with a respective field. Then, a patient, or other recipient, that receives the medical instrument form can populate one or more respective fields in response to the question. Alternatively, or in addition, one or more fields of the medical instrument form may be automatically populated by the creator of the medical instrument form, the transmitter of the medical instrument form, or both. The non-biometric data may include, for example, the procedure type (e.g., knee surgery, wrist surgery, or the like), status (e.g., pre-operation, 6 months post operation, or the like), institution where procedure was performed (e.g., ABC Hospital), or the professional's name who performed the procedure (e.g., Dr. Smith, Dr. Kim, or the like). The types of non-biometric data described with respect to medical instrument forms 102, 103, 104, 105, 106, 107, 108 are merely exemplary. Accordingly, it is contemplated that other types of non-biometric data may be solicited using a particular medical study instrument.

Medical instrument forms 102, 103, 104, 105, 106, 107, 108 may also include one or more fields that have been populated to include biometric data that is indicative of the patient's health. The biometric data may be obtained my providing multiple questions in a medical instrument form that each correspond to a respective field. Then, a patient, or other recipient, that receives the medical instrument form can populate the one or more respective fields in response to a question that corresponds to each field. Alternatively, or in addition, one or more fields of the medical instrument form may be automatically populated by the creator of the medical instrument form, the transmitter of the medical instrument form, or both. The biometric data may include, for example, responses to one or more inquiries regarding whether the patient is experiencing any pain or discomfort, responses to inquiries regarding specific areas of the patient's body associated with the discomfort, responses to one or more inquiries regarding any signs of infection, responses to one or more inquiries regarding any illness or side effects, responses to one or more inquiries regarding the patient's overall level of comfort, or the like.

The data extraction unit 110 is configured to extract data from one or more fields of obtained medical study instruments 102, 103, 104, 105, 106, 107, 108. For instance, the data extraction unit 110 can analyze each obtained medical study instrument to identify one or more fields containing data that corresponds to respective fields maintained by the medical study instrument index 120. For instance, the data extraction unit 110 can analyze an obtained medical study instrument in order to identify a procedure field in the medical study instrument. The data extraction unit 110 can extract the data that populates the procedure field of the medical study instrument, create a new entry in the medical study instrument index 120 corresponding to the medical study instrument from which the data was extracted, and store the extracted data in the procedure field of the created index entry in the medical study instrument index 120. In some instances, an index entry that corresponds to a medical study instrument being analyzed by the data extraction unit 110 may already exist in the medical study instrument index. In such instances, the data extraction unit 110 may only extract the relevant data from the medical study instrument and store the extracted data in a corresponding field of the medical study instrument index 120 without the need to create a new index entry. The use of the data extraction unit 110 to identify and select only a subset of the data contained within obtained medical study instruments in the medical study instrument index results in an optimization of processing power since only the extracted data needs to be searched for each medical study instrument and not the entire medical study instrument file. The data extracted by the extraction unit 110, and used to create the medical study instrument index 120 maintained by the search engine system 100, may be transmitted to the one or more server computers hosting the search engine system 130 via one or more networks such as a LAN, WAN, a cellular network, the Internet, or the like.

The search engine system 100 includes one or more server computers that maintain a medical study instrument index 120 that is generated based, at least in part, on data received from the data extraction unit 110. The medical study instrument index 120 can be used to access relevant data extracted from multiple disparate medical study instruments 102, 103, 104, 105, 106, 107, 108. Alternatively, or in addition, the medical study instrument index 120 can be used to access a patient health score 117 that is generated based on data extracted from the obtained medical study instruments. The medical study instrument index 120 can be conceptually modeled as a logical table including a plurality of logical rows and a plurality of logical columns. Each logical row of the medical study instrument index 120 such as logical rows 121, 122, 123, 124, 125, 126, 127, 128 corresponds to a subset of relevant information extracted from a particular medical study instrument 101, 102, 103, 104, 105, 106, 107, 108 by the data extraction unit 110. Each logical column of the medical study instrument index 120 conceptually defines a particular data attribute of a particular medical study instrument associated with a particular logical row.

In one implementation, the one or more fields selected for inclusion in the medical study instrument index 120 are indexed to achieve certain gains in efficiency. For instance, one or more index fields such as the procedure field 120a can be selected for inclusion in the medical study instrument index 120 because the one or more fields are candidates for frequent searches. By way of example, data in the medical study instrument index may be frequently searched based on procedure 120a, status 120b, and institution 120c as part of the process for determining the average patient score for patients who are 6-months removed from knee surgery at a particular hospital. Alternatively, data in the medical study instrument index may be frequently searched based on procedure 120a, status 120b, and prof. name 120d as part of the process for determining the average patient score for patients who are 6-months removed from knee surgery performed by a particular health professional, health provider, or the like. Alternatively, data in the medical study instrument index may be frequently searched based on procedure 120a and status 120b as part of the process for determining the average patient score for patients 6-months removed from having knee surgery independent of institution or professional who performed the knee surgery.

The aforementioned searches may be performed on the medical study index 120 in order to identify a set of one or more index entries that satisfy the constraints of the search. Then, each identified index entry can be used to obtain other data extracted from a respective medical study instrument that corresponds to each respective identified index entry. In one implementation, the identified index entries can be used to obtain a respective patient health score 117 that were each derived from data extracted from a respective medical study instrument that corresponds to each identified index entry.

Each index entry 121, 122, 123, 124, 125, 126, 127, 128 of the medical study instrument index 120 includes data that has been extracted from a respective medical study instrument 101, 102, 103, 104, 105, 106, 107, 108. For instance, the index entry 121 corresponds to the medical study instrument index 101. Similarly, for example, the index entry 122 corresponds to the medical study instrument 102. In one implementation, each entry of the medical study instrument index may include a procedure type 120a, a status 120b, an institution 120c where the procedure occurred, and a professional's name 120d that performed the procedure. The procedure type 120a may include the portion of a patient's body (e.g., knee, wrist, hand, foot, etc.) on which a procedure was performed or a portion of a patient's body a procedure is to be performed on in the future. Alternatively, or in addition, the procedure type 120a may include the name of a medical procedure. The status 120 may provide an indication as to a time period that the corresponding medical study instrument was related to (e.g., pre-op or pre-procedure, 6-months after the procedure, 12 months after procedure, 18 months after the procedure, or the like). The institution 120c may provide an indication as to the institution that performed the procedure. The professional name 120d may provide an indication as to the medical professional, medical provider, or the like who performed the procedure. Though the example here specifies a number of fields that may be included in the medical study instrument index, the present disclosure need not be so limited. Instead, medical study instrument indices can be employed that include more fields or less fields so long as the medical study instrument index entry includes the procedure field 120a.

Each respective medical study instrument index entry can be used to retrieve a patient health score 117. For instance, the patient health score 117a may be generated based on data extracted from a medical study instrument 101 and be indexed by index entry 121. As a result, the index entry 121 can be used to retrieve, or otherwise obtain, the patient score 117a.

The patient health score 117 may provide an indication of the current health state of the patient at the time the patient populated the fields of the corresponding medical study instrument. The patient health score 117 may be a value that is based on the data input into one or more fields of a medical study instrument by a patient who received a medical study instrument. In one implementation, the patient health score 117 may be based on biometric data used to populate a medical study instrument. The data input by a patient into one or more fields of a medical study instrument may be indicative of the patient's experience with a medical facility, medical professional, or the like in relation to a particular procedure. In some instances, the patient health score may be derived from one or more component scores such as a quality score, a satisfaction score, a cost score, and/or the like. For example, the patient health score may be an average of the one or more components scores. Alternatively, in some instances, the patient health score may be a weighted average with one or more components scores being assigned a higher (or lower) weight based on the importance of the particular component scores in representing the patient's overall health. Regardless of formulation, however, the patient health score 117 can be any numerical value that can be used to compare the patient's pre-procedure well-being with the patient's post-procedure well-being in a manner that can be used to evaluate a medical institution's or a medical professional's performance in delivering the medical procedure.

The search engine system 100 also includes a query processor 130. The query processor 130 receives query parameters from one or more user devices via one or more networks, generates one or more queries based on the received parameters, and executes the generated queries. In one implementation, the query parameter may include at least one or more particular procedure types. Alternatively, or in addition, the query parameters may include parameters directed towards other fields maintained by the medical study instrument index 120. For instance, the queries processed by the query processor 130 may include a procedure parameter and a status parameter. In one implementation, execution of a query by the query processor 130 may include searching the medical study instrument index 120 to identify each of the index entries that satisfy the constraints imposed by the parameters of the received query. The identified index entries can then be used to obtain patient health scores for each identified index entry.

A graphical user interface may be provided that includes one or more fields to receive query parameters. In one implementation, the graphical user interface may include a general search field that is configured to receive free-form text strings input by a user. In such instances, the graphical user interface may be part of an application that is preconfigured to provide, for example, pre-procedure and post procedure values for a received text string that is input into the general search field as a procedure. For example, in such an implementation, a user may input a procedure type such as "wrist," and the application may instruct the query processor 130 to generate a query to identify index entries corresponding to "wrist" procedures, and then use the data in the identified index entries to obtain patient scores that can be used to generate an average patient score for all known patients prior to a wrist procedure and also generate an average patient score for all known patients 6-months after wrist procedure. The average pre-procedure score and the average post procedure score may then be output for display on a user interface.

Alternatively, or in addition, the graphical user interface may provide multiple search fields that are configured to receive specific input criteria. For instance, the graphical user interface may provide a first field that is configured to receive a procedure type, one or more check boxes that each correspond to a particular status, a third field that is configured to receive an institution, and a fourth field that is configured to receive a professional name. Alternatively, or in addition, the graphical user interface may include other input fields including, for example, a date input field, a representative patient score type field, or the like. The date input field may limit the index entries obtained in response to a search to a particular time period, based on the data provided as input to the date input field. The representative patient score type field may specify the type of calculation to be performed to generate a representative patient score for pre-procedure and post-procedure comparisons based on the patient health scores obtained for each index entry responsive to a search query. Representative patient score types may include, for example, an average score, a median score, a mean score, or the like. The graphical user interface may include more, less, or different fields that are based on the fields of the medical study instrument index 120, the type of patient score calculation to be performed, or the like. Once inputs to each field are submitted, the query processor 130 may generate a query based on the inputs to each field, execute the query against the medical study instrument index 120 to identify a set of relevant index entries, calculate requested pre-procedure representative patient health scores and post-procedure representative health scores using patient scores obtained using the identified index entries, and then output the calculated scores for display on the graphical user interface of a user device.

For instance, a user may use a graphical user interface to input "knee" into the procedure type field, activate check boxes associated with a pre-procedure representative patient score and a post-procedure representative patient score, input "ABC Hospital into the institution field, not specify a date range, and provide input indicating that the representative patient score should be an average score. Once such parameters are submitted, the query processor 130 may generate one or more queries necessary to obtain information requested by the user to evaluate ABC Hospital's knee procedures. In this example, multiple queries may be generated and executed. For instance, the query processor may generate and execute a first query to determine the pre-procedure representative patient score for the received parameters and a second query to determine the post-procedure representative patient score for the received parameters. By way of example, with reference to the medical study instrument index 120 of FIG. 1, the representative pre-procedure score for knee procedures at ABC Hospital may be "42.5" (e.g., 43+42/2=42.5) while the representative post-procedure score for patients 6-months removed from knee procedures at ABC Hospital may be "54" (57+51/2=54). The respective representative patient scores may then be provided for display on a user device. Based on the displayed scores, it can be determined that patients who had knee procedures performed at ABC Hospital were better off after the knee procedure than they were prior to the knee procedure because patients, on average, tend to have a higher patient health score after the knee procedure than they did before the knee procedure.

As another alternative form of input, a graphical user interface of a user device may include a fast forward selectable icon that facilitates retrieval of a representative patient score that is associated with a different status for a predetermined procedure. For instance, in the aforementioned example, a pre-procedure score for knee procedures at ABC hospital was determined to be 42.5 and a post procedure score for patients that are 6-months removed from a knee procedure at ABC Hospital was determined to be 54. While such values may be displayed on a graphical user interface of a user device after the initial query that was used to generate those values, the same graphical user interface may display a fast forward selectable icon to modify the post operation "status" associated with this knee procedure at ABC Hospital.

In response to a selection of the fast forward selectable icon, an instruction may be transmitted to the query processor to generate a revised query that can identify index entries that correspond to all patients 12 month removed from knee surgery at ABC Hospital. The query processor may receive the identified index entries, obtain the patient scores 117 that correspond to the identified index entries, use a post processing unit to determine a representative patient score based on the obtained patient scores 117, and provide the representative patient score for display on the user device.

Note that the fast forward selectable icon that modifies the "status" parameter of a query associated with a predetermined procedure type can be configured to modify the status parameter to include any post-procedure time period. For instance, assuming the index maintains index entries corresponding to medical study instruments completed monthly after a patient's procedure, the fast forward selectable icon that modifies the "status" parameter of the query can incrementally retrieve representative patient scores at incremental time periods for each selection. For instance, each selection of the fast forward selectable icon could initiate the determination of a representative patient score at 6-months removed form a procedure, at 7-months removed from the procedure, 8-months removed from the procedure, or the like. With each selection, the newly determined representative patent score may replace the previously displayed representative patient score for the previous status period. Alternatively, the representative patient score for the new incremental time period may be display in addition to the representative patient score for the prior status period. For example, the prior status period representative patient score and the new incremental status period representative score may be displayed as entries in a table, chart, graph, or the like.

In a similar manner, a different rewind selectable icon could be configured to initiate the determination of representative patient scores in descending time periods such as from 8-months to 7-months to 6-months for each respective selection of the different rewind selectable icon. Such functionality may be particularly useful in those implementations that replace the first status period's representative patient score with the representative patient score from the new incremental status period when the fast forward selectable icon is selected.

The query processor 130 may utilize a post-processing unit in order to generate the representative patient scores. For instance, the query processor 130 may execute a search that identifies a set of index entries that are responsive to the search (e.g., a set of index entries have a procedure type "knee"). Next, the patient scores referenced by each respective index entry that is responsive to the query may be obtained for post-processing without retrieving the complete medical study instrument that corresponds to each respective index entry. In some implementations, the complete medical study instrument is not stored by the search engine system 100 after being processed by the data extraction engine 110. For each type of representative patient score requested by a user, the post-processing unit may calculate the requested type of representative patient score. For instance, post-processing unit may calculate the average patient health score for all knee procedures prior to the knee procedure. Similarly, the post-processing unit may calculate the average patient health score for all knee procedures 6-months after a knee procedure has been performed. Then, the calculated scores may be provided for display on a graphical user interface of a user device.

In some implementations, an optimized medical study instrument index can be periodically generated in order to substantially reduce the amount of post processing required by the query processor 130. An optimized medical study instrument index can be generated, in one example, by first clustering the data in the medical study instrument index 120 based on at least procedure type 120*a* and status 120*b*. Once the data is clustered, the system 100 may calculate an average patient score for each procedure—status cluster. For example, one procedure—status cluster may include all index entries related to a patient's status pre-operation prior to a particular knee procedure. Once clustered, the system 100 may calculate a representative patient health score based on the patient health scores 120*e* referenced by each clustered index entry. By way of example, an average representative patient health score may be requested by a user. With reference to the medical study instrument index 120, for example, an average patient health score for patients prior to a knee procedure is 42.5 (e.g., 43 from index entry 121+42 from index entry 125/2=42.5). In such instances, the optimized medical study instrument index may only store an index entry that references an average patient score of 42.5 instead of two separate index entries 121 and 125 that each reference patient scores of 43 and 42, respectively. Using an optimized index, the query processor 130 merely needs to request an index entry corresponding to a particular procedure—status combination, and then obtain the representative patient score using the identified index entry.

The search engine system 100 can be used in multiple ways to evaluate the performance of a medical institution, a medical professional/provider, or the like. A few different examples are provided below with reference to FIG. 1

A user named Bob may, for example, enter query parameters 150 into an application 140 (e.g., a healthcare benchmarking application) running on a user device that requests an average pre-procedure score and an average post-procedure score for all procedures at "ABC Hospital." After entering the query parameters 150, Bob may instruct the application 140 running on the user device to transmit 152 the query parameters 150 to the query processor 130 via one or more networks such as a LAN, a WAN, a cellular network, the Internet, or the like. The query processor may generate a query based on the query parameters 150, and execute 135 the generated query against the medical study instrument index 120. Alternatively, in some implementations, the query may be executed against an optimized version of medical study instrument index 120. The query processor 130 may receive 135 a set of one or more index entries from the medical study instrument index 120, or an optimized version thereof. A post-processing unit of the query processor may determine the one or more representative patient scores requested by Bob. Then, the query processor 130 may transmit 154 the one or more representative patient scores via one or more networks such as a LAN, a WAN, a cellular network, the Internet or the like to Bob's user device for display using a graphical user interface provided by the application 140 running on Bob's user device. The average patient pre-procedure score 140a for ABC Hospital is 42.5 whereas the average patient score 6-months 140b removed from procedure is 43.5. Accordingly, it can be determined that when a patient goes to ABC Hospital for a procedure, the patient tends to be better off after the patient receives procedure from ABC Hospital than the patient was before the patient sought procedure from ABC Hospital since the average patient score is higher post-procedure than the average patient score pre-procedure.

Similarly, another user named Steve may, for example, enter query parameters 160 into an application 142 (e.g., a healthcare benchmarking application) running on a user device that requests an average pre-procedure score and an average post-procedure score for all "Knee" procedures at "ABC Hospital." After entering the query parameters 160, Steve may instruct the application 142 running on the user device to transmit 162 the query parameters 160 to the query processor 130 via one or more networks such as a LAN, a WAN, a cellular network, the Internet, or the like. The query processor may generate a query based on the query parameters 160, and execute 135 the generated query against the medical study instrument index 120. Alternatively, in some implementations, the query may be executed against an optimized version of medical study instrument index 120. The query processor 130 may receive 135 a set of one or more index entries from the medical study instrument index 120, or an optimized version thereof. A post-processing unit of the query processor may determine the one or more representative patient scores requested by Steve. Then, the query processor 130 may transmit 164 the one or more representative patient scores via one or more networks such as a LAN, a WAN, a cellular network, the Internet, or the like to Steve's user device for display using a graphical user interface provided by the application 142 running on Steve's user device. The average patient pre-procedure score 142a for knee procedures at ABC Hospital is 42.5 whereas the average patient score 6-months 142b removed from procedure is 54. Accordingly, it can be determined that when a patient goes to ABC Hospital for a knee procedure, the patient tends to be better off after the patient receives the knee procedure from ABC Hospital than the patient was before the patient sought knee procedure from ABC Hospital since the average patient score is higher post-procedure than the average patient score is pre-procedure.

Bob and Steve used the search engine system 100 above in an effort to search and retrieve data that can be used to evaluate a medical institution, medical provider, or the like. However, the search engine system 100 also has other benefits. For instance, a medical professional such as Dr. Smith, can use the search engine system 100 to evaluate his own practice.

Dr. Smith may be a doctor that has experience performing knee and wrist procedures. From time to time, Dr. Smith may want to self-evaluate his practice in view of the multiple procedures he has performed. Dr. Smith could evaluate his practice across the board in similar manner as the search performed by Bob. That is, Dr. Smith could seek a general, universal search of all his patients, and all of his procedures and determine that his average patient pre-procedure score is 42 (e.g., 43+42+41/3=42) and his average patient post-procedure score is 48.6 (57+51+38/3=48.6), based on the data obtained using the medical study instrument index 120. Such numbers indicate that, on average, Dr. Smith's patients are, on average, better off after he performs a procedure on them than they were before Dr. Smith performed a procedure on them. However, Dr. Smith can use the search engine system 100 to analyze his practice in a more specific manner in an effort to identify areas of his practice where he may improve.

For instance, Dr. Smith may enter query parameters 170 into an application 144 (e.g., a healthcare benchmarking application) running on a user device that requests an average pre-procedure score and an average post-procedure score for all "knee" procedures performed by "Dr. Smith." After entering the query parameters 170, Dr. Smith may instruct the application 144 running on the user device to transmit 172 the query parameters 170 to the query processor 130 via one or more networks such as a LAN, a WAN, a cellular network, the Internet, or the like. The query processor may generate a query based on the query parameters 170, and execute 135 the generated query against the medical study instrument index 120. Alternatively, in some implementations, the query may be executed against an optimized version of medical study instrument index 120. The query processor 130 may receive 135 a set of one or more index entries from the medical study instrument index 120, or an optimized version thereof. A post-processing unit of the query processor may determine the one or more representative patient scores requested by Dr. Smith. Then, the query processor 130 may transmit 174 the one or more representative patient scores via one or more networks such as a LAN, a WAN, a cellular network, the Internet, or the like to Dr. Smith's user device for display using a graphical user interface provided by the application 144 running on Dr. Smith's user device. The average patient pre-procedure score 144a for knee procedures performed by Dr. Smith is 42.5 whereas the average patient score 6-months 144b removed from procedure is 54. Accordingly, Dr. Smith can conclude that he is performing knee procedures at a high level because his patients tend to be much better off after the patient receives a knee procedure from Dr. Smith than the patient was before the patient sought a knee procedure from Dr. Smith since the average patient score is higher post-procedure than the average patient score is pre-procedure.

Similarly, Dr. Smith may enter different query parameters 180 into the same application 144 running on the user device that requests an average pre-procedure score and an average post-procedure score for all "wrist" procedures by "Dr. Smith." After entering the query parameters 180, Dr. Smith may instruct the application 144 running on the user device to transmit 182 the query parameters 180 to the query processor 130 via one or more networks such as a LAN, a WAN, a cellular network, the Internet, or the like. The query processor may generate a query based on the query parameters 180, and execute 135 the generated query against the medical study instrument index 120. Alternatively, in some implementations, the query may be executed against an optimized version of medical study instrument index 120. The query processor 130 may receive 135 a set of one or more index entries from the medical study instrument index 120, or an optimized version thereof. A post-processing unit of the query processor may determine the one or more representative patient scores requested by Dr. Smith. Then, the query processor 130 may transmit 184 the one or more representative patient scores via one or more networks such as a LAN, a WAN, a cellular network, the Internet, or the like to Dr. Smith's user device for display using a graphical user interface provided by the application 144 running on Dr. Smith's user device. The average patient pre-procedure score 144c for wrist procedures by Dr. Smith is 41 whereas the average patient score 6-months 144d removed from the wrist procedure is 38. Accordingly, Dr. Smith can conclude that he is performing wrist procedures at a low level because his patients tend to be slightly worse off after the patient receives a wrist procedure from Dr. Smith than the patient was before the patient sought the wrist procedure from Dr. Smith since the average patient score is lower post-procedure than the average patient score is pre-procedure. In view of such a determination, Dr. Smith can take measures to improve his performance so that he better serves his patients.

Figure 2:
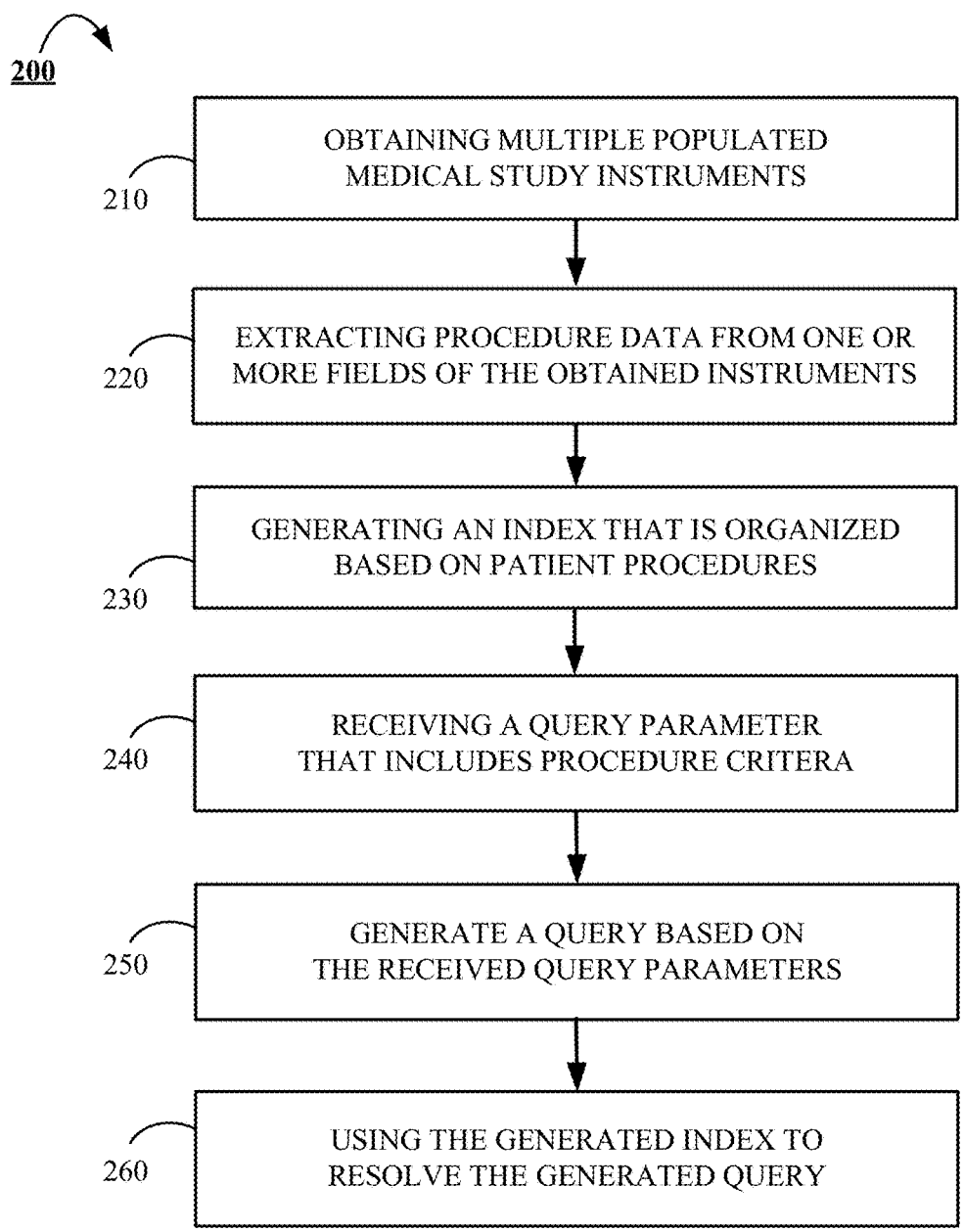
FIG. 2 is a flowchart of an example of a process for generating and accessing a medical study instrument index organized by procedure type.

FIG. 2 is a flowchart of an example of a process 200 for generating and accessing a medical study instrument index organized by procedure type. For convenience, the process 200 will be described as being performed by a system. For example, the search engine system 100 discussed above can perform the process 200 to generate and access a medical study instrument index that is organized by procedure type.

The process 200 begins when the search engine system 100 obtains one or more multiple medical study instruments. The system 100 may obtain a medial study instrument in a variety of different ways. For example, the system 100 may request a set of one or more populated medical study instruments from a remote third party computer that is connected to system 100 via one or more networks such as the Internet. Alternatively, or in addition, the system 100 may, for example, receive a set of one or more populated medical study instruments that has been uploaded to the system 100 from one or more remote computers. In one example, a patient may upload a populated medical study instrument to the system 100 after the patient populates the medical study instrument.

The process 200 may continue at stage 220 when system 100 extracts procedure data from one or more fields of the obtained medical study instruments. The system 100 can analyze the obtained medical study instruments in order to identity one or more fields that correspond to fields defined by the medical study instrument index. For instance, in one implementation, the system 100 may extract a procedure type, a status, an institution name, and a professional name from each obtained medical study instrument. In another implementation, however, the system 100 may extract at least the procedure type. For example, the system 100 may analyze the medical study instrument to determine that the procedure type the patient received was related to the patient's "knee," and then extract the data "knee" from the procedure type field of the medical study instrument. The system may associate the generated index entry with a patient health score that corresponds to the obtained medical study instrument from which the data for the index entry was extracted. The patient health score may be generated based on the data biometric data included in the obtained medical study instrument used to generate the index entry. The generated index entry can be used to obtained the generated patient health score. Though specific examples of the type of data that may extracted from a medical study instrument are described, data may also be extracted from additional fields or less fields at stage 220, as necessary.

At stage 230, the system 100 may generate an index that is organized on patient procedure type. An index may be generated based on procedure type by aggregating all the generated index entries that include the extracted data into a logical storage area that can be efficiently searched. The index may be organized by procedure type because each index entry of the generated index includes an indexed procedure type field that may be searched. A previously generated index that is organized by procedure type may be updated by following stages 210 through 230. However, at stage 230, any newly generated index entries may be added to the existing index.

At stage 240, receiving one or more query parameters that include a procedure type. For instance, a user may submit a query parameter into an application search input box that includes the word "knee." The system 100 may obtain the one or more received query parameters and generate 250 a query based on the one or more received query parameters. Then, the system 100 may be configured to use 250 the index that is organized by procedure type to determine a pre-procedure representative score, a post-procedure representative score, or both. The system 100 use the index that is organized by procedure type by executing a query that is generated based on the received procedure query parameters against the index that is organized by procedure type, and identifying one or more index entries that satisfy the constraints of the query. The identified index entries can be used to obtain the patient health scores, which can be used to calculate the representative scores.

In some implementations, the application may be configured to automatically obtain both the pre-procedure representative patient score and a post-procedure representative patient sore based on the receipt of a procedure type query parameter. However, in other implementations, a user may alter the current state of one or more checkboxes, radio buttons, fields or the like in order to instruct the application to obtain only one of the representative patient scores or another type of representative patient score.

Figure 3:
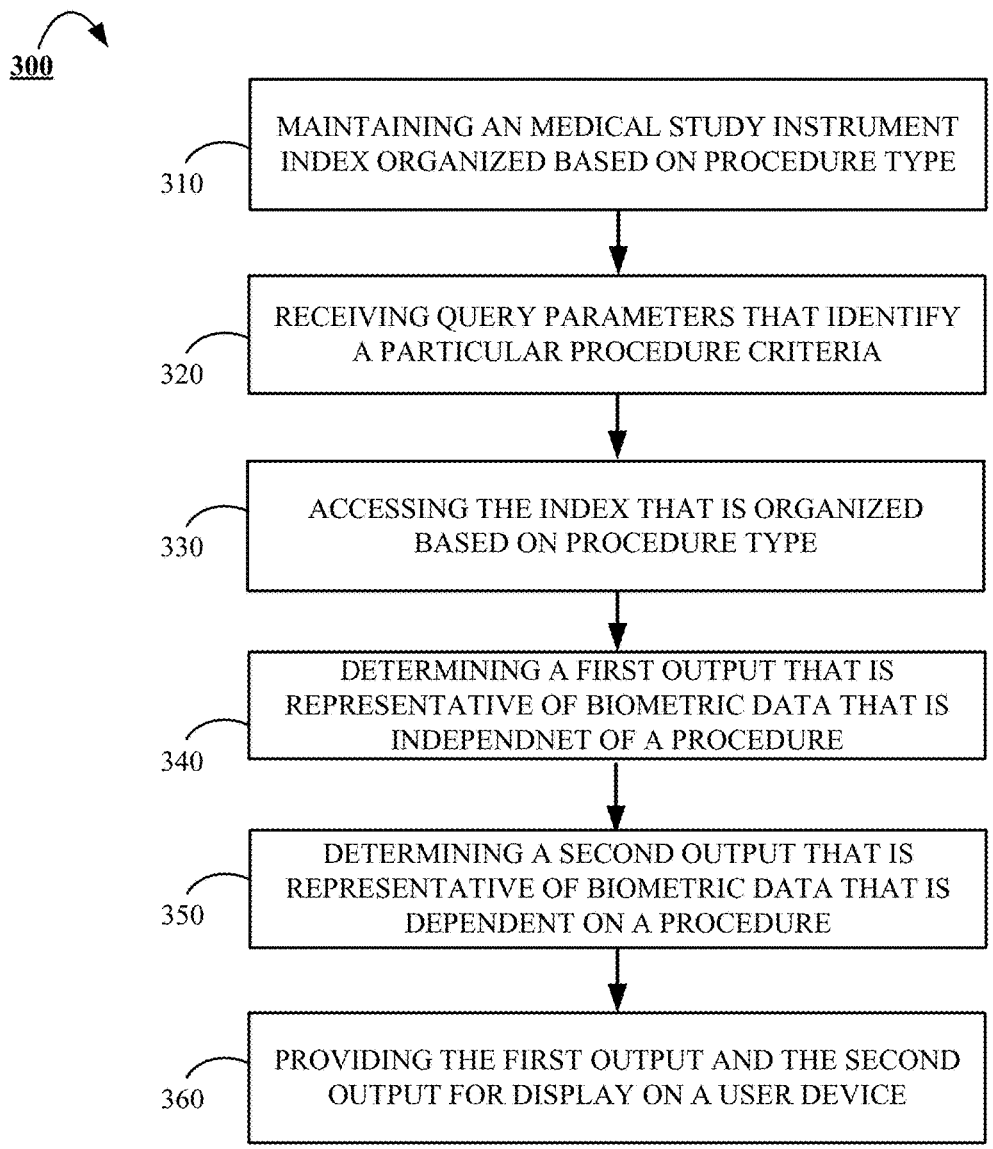
FIG. 3 is a flowchart of an example of a process for evaluating a healthcare entity's performance using a medical study instrument index organized by procedure type.

FIG. 3 is a flowchart of an example of a process 300 for evaluating a healthcare entity's performance using a medical study instrument index organized by procedure type. For convenience, the process 300 will be described as being performed by a system. For example, the search engine system 100 discussed above can perform the process 300 to generate and access a medical study instrument index that is organized by procedure type.

The process 300 begins with the search engine system 100 maintaining a medical study instrument index that is organized by patient procedure type. A patient procedure type may include, for example, a knee procedure, a wrist procedure, a back procedure, or the like. Alternatively, or in addition, patient procedure types may be described in more detail such as knee cap replacement, ACL surgery, MCL surgery, or the like. Maintaining the medical study index may include creating, deleting, or updating one or more index entries.

At stage 320 the system 100 may receive one or more query parameters that identify a particular procedure criteria. For instance, the system 100 may receive query parameters that include the keyword "knee." The received query parameters may be received by a query processor, and transformed into a structured query that is suitable for searching the medical study instrument index maintained by the system 100. In one implementation, the received query parameters may be associated with a procedure benchmarking request. The benchmarking request may seek information that can be used to evaluate a particular institution's or a particular provider's history with respect to a the performance of the identified procedure.

The system 100 may access 330 the medical study instrument index that is organized based on procedure type. In one implementation, the system 100 may process the generated query against the medical study instrument index in order to identify a set of index entries that satisfy the procedure criteria identified in the query. The set of index entries can be used to obtain respective patient health scores referenced by each respective index entry of the set of index entries. In such instances, the system may use a post-processing unit to process the patient health scores into a representative patient score. Alternatively, the system 100 may access an optimized version of the medical study instrument. In such instances, the system 100 may merely obtain the representative patient score from the identified index entry.

At stage 340 the system determines a first output that is representative of biometric data that is independent of the procedure identified in the received query parameters. In one implementation, the first output may be representative biometric data that is indicative of multiple patient's health prior to each respective patient receiving the procedure identified in the received query parameters. The biometric data may include, for example, a representative patient health score such as an average of a number of patients' health scores prior to the patient's receiving the procedure.

At stage 350 the system determines a second output that is representative of biometric data that is dependent of the procedure identified in the received query parameters. In one implementation, the second output may be representative biometric data that is indicative of multiple patient's health after each respective patient receives the procedure identified in the received query parameters. The biometric data may include, for example, a representative patient health score such as an average of a number of patients' health scores after the patient's received the procedure. For example, the representative post-treatment health score may be 6-months after the procedure, 12 months after the procedure, 18 months after the procedure, or the like.

The system may provide the first output and the second output for display on a user device at stage 360. The first output and the second output may be displayed in any number of ways. For instance, the first output and the second output may be displayed using a chart, bar graph, table, or the like. Though the first output and the second output may be provided for display on a user device, other ways of outputting the first output and the second output fall with the scope of the subject matter disclosed by this specification. For instance, the first and second output may be output via an audio message using a speaker of the user device. Alternatively, or in addition, the first and second output may be transmitted in a report to a user via email, SMS message, MMS message, or the like.

Figure 4:
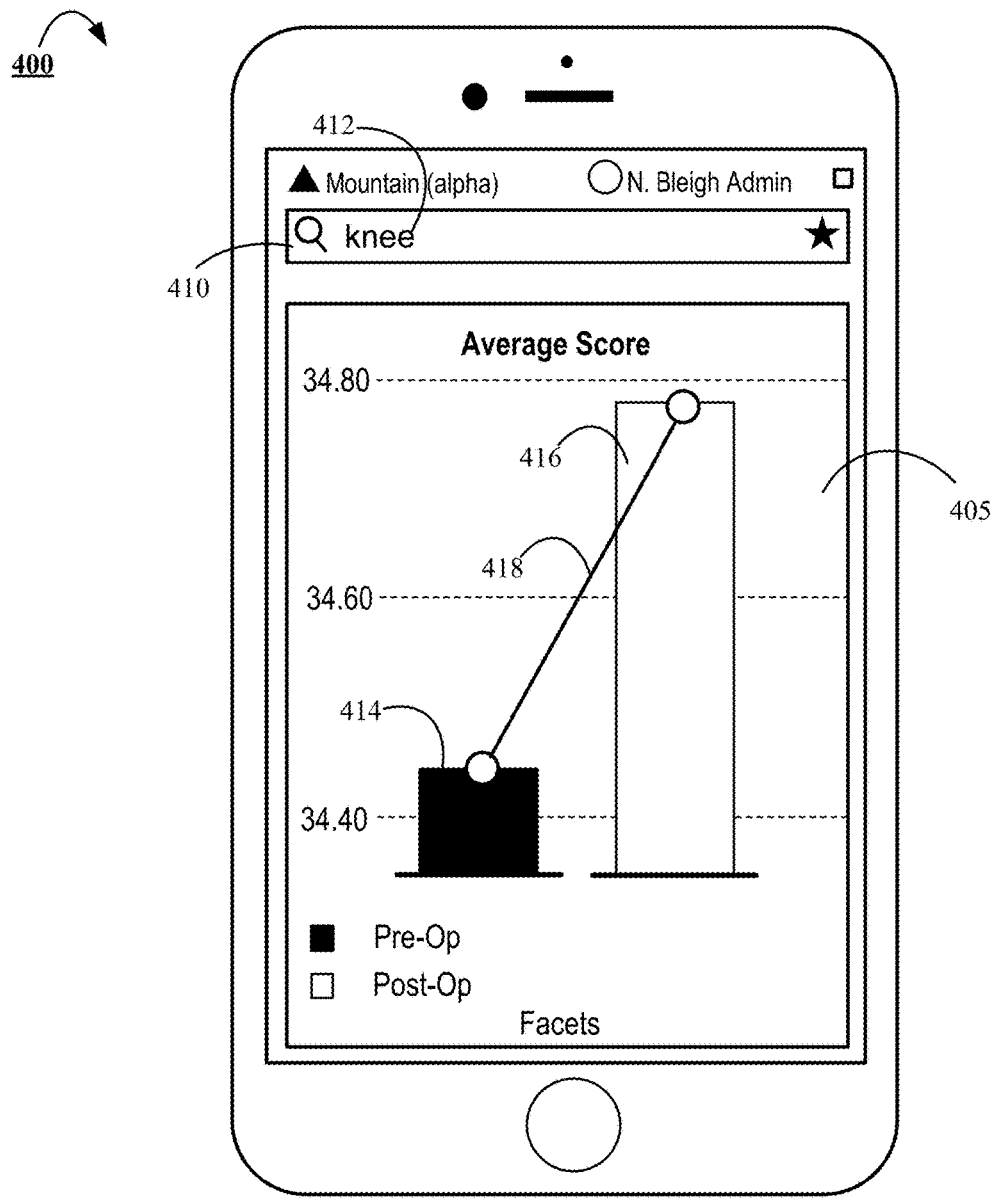
FIG. 4 is a depiction of an example of a graphical user interface for displaying data in a chart derived from search results identified using a medical study instrument index.

FIG. 4 is a depiction of an example of a graphical user interface 405 for displaying data in a chart derived from search results identified using a medical study instrument index.

A user device 400 may run a mobile application that is configured to receive benchmarking requests. Alternatively, the user device may access a web application using a browser that is configured to receive benchmarking requests.

The search box 410 is configured to receive query parameters 412 that include procedure criteria such as "knee." The search engine system such as system 100 receives the input query parameters 412, generates one or more queries based on the received query parameters, and then determines a first output represented by a first bar graph 414 and a second output that is represented by the second bar graph 416 on the graphical user interface 405. In this example, the first output is indicative of an average patient score prior to a knee procedure and the second output is indicative of an average patient score after the knee procedure. The trend line 418 indicates that, on average, patient's health, as represented by an average patient health score, tends to improve after the knee procedure.

Figure 5:
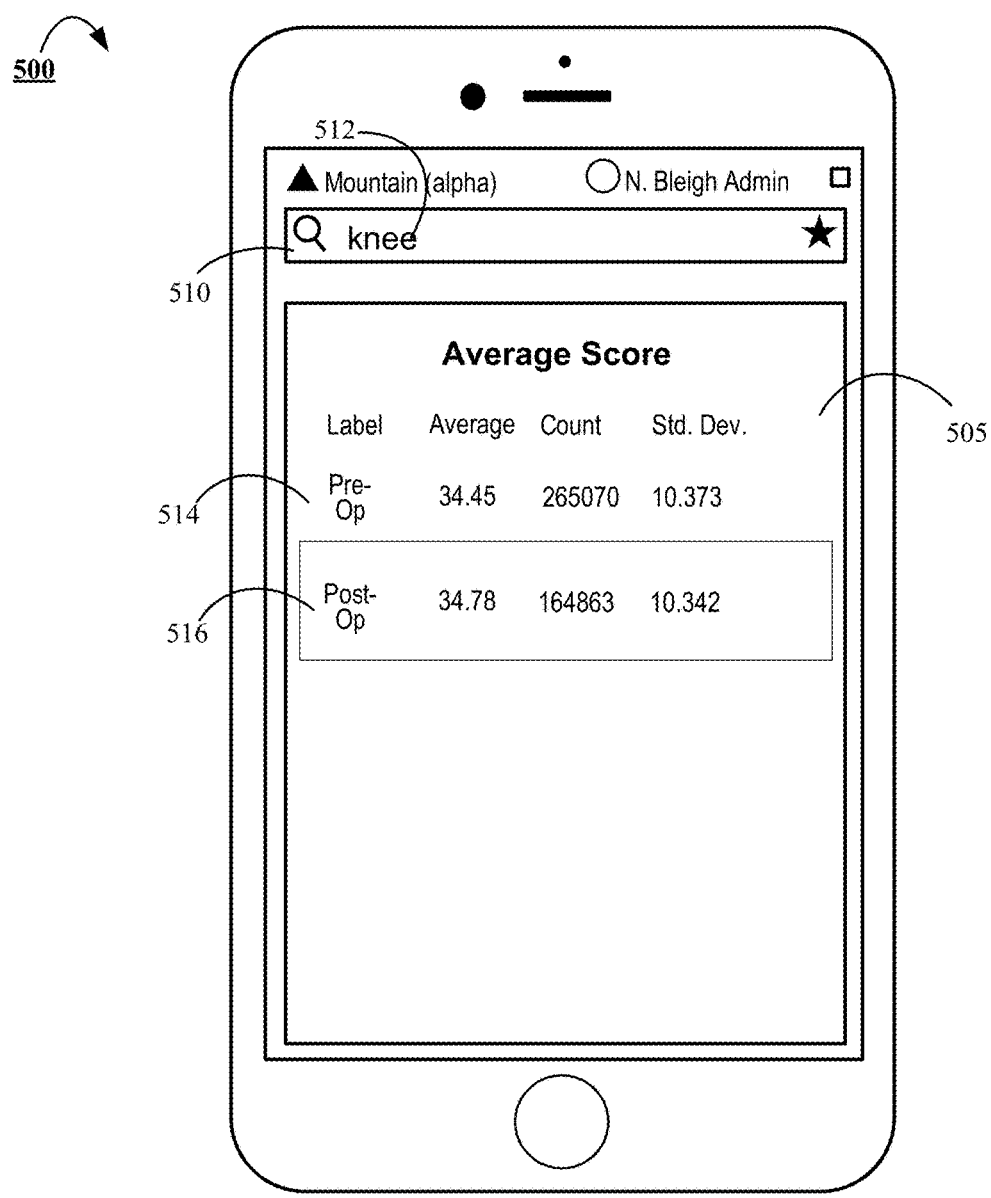
FIG. 5 is a depiction of an example of a graphical user interface for displaying data in a table derived from search results identified using a medical study instrument index.

FIG. 5 is a depiction of an example of a graphical user interface 505 for displaying data in a table derived from search results identified using a medical study instrument index.

A user device 500 may run a mobile application or web application that is the same, or substantially similar to, the mobile application or web application described with respect to the example of FIG. 4. For instance, the mobile application may provide a search box 510 that is configured to receive query parameters 512 that include procedure criteria such as "knee." A search engine system such as system 100 receives the input query parameters 512, generates one or more queries based on the received parameters, and then determines a first output and a second output. Though the first output and the second output determined by the mobile application running on device 500 is the same as the first output and the second output determined by the mobile application running on device 400, the graphical user interface 505 that is associated with the mobile application running on device 500 outputs the first output 514 and the second output 516 in a different format. For instance, the mobile application running on user device 500 outputs the first output 514 and the second output 516 in a table format with multiple rows. In a similar manner to the example of FIG. 4, user device 500 provides a user interface 505 where the first output is indicative of an average patient score prior to a knee procedure and the second output is indicative of an average patient score after the knee procedure.

Figure 6:
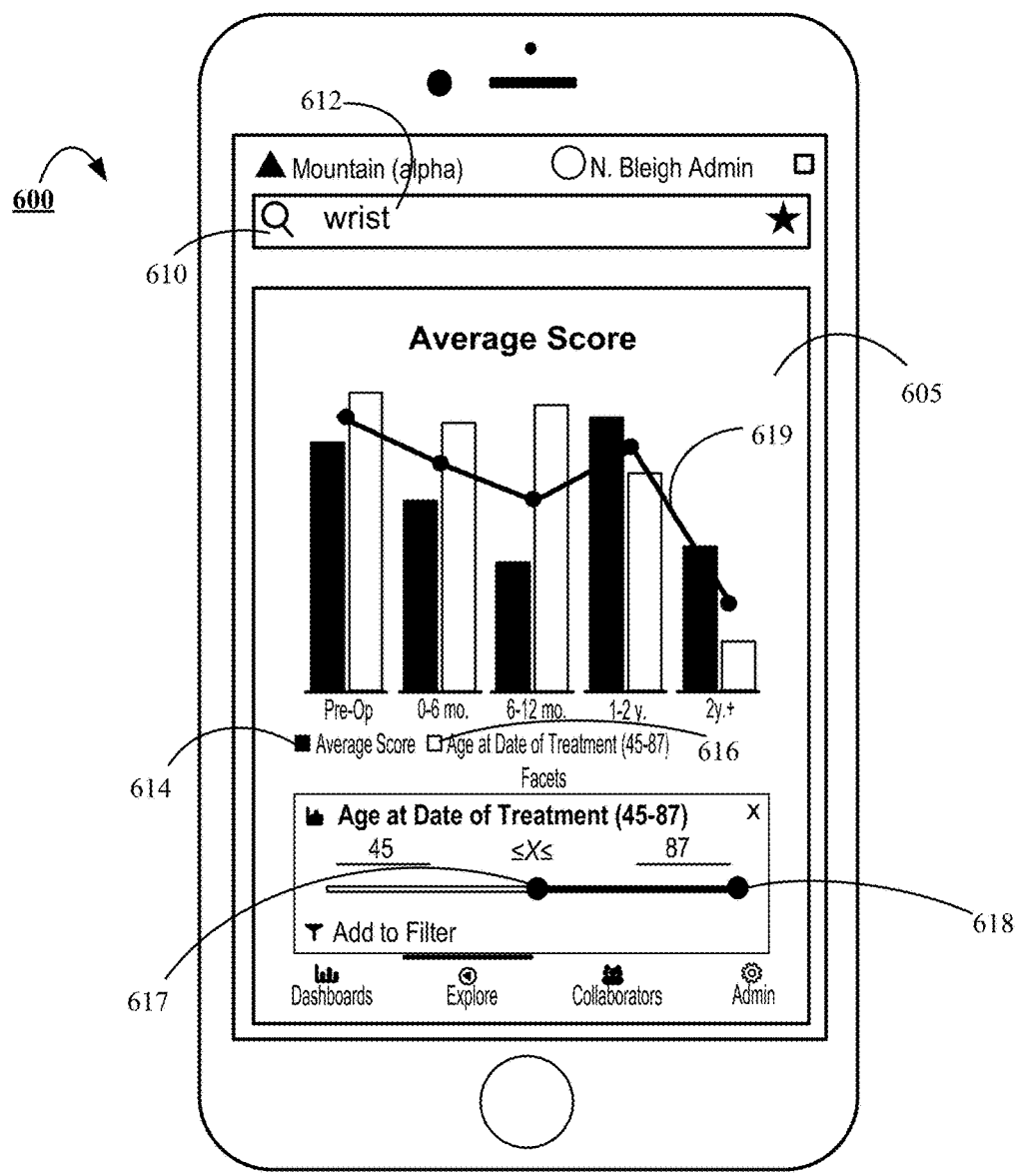
FIG. 6 is a depiction of another example of a graphical user interface for display data in a chart derived from search results identified using a medical instrument index.

FIG. 6 is a depiction of another example of a graphical user interface 605 for display data in a chart derived from search results identified using a medical instrument index.

A user device 600 may run a mobile application that is configured to receive benchmarking requests. For instance, the search box 610 is configured to receive query parameters 612 that include procedure criteria such as "wrist." The search engine system such as system 100 receives the input query parameters 612, generates one or more queries based on the received query parameters, and then determines multiple outputs that are represented by bar graphs. The output values include two different types of data. The first type of data is an average patient health score for respective time periods relative to the procedure identified in the query parameters 612. For instance, the first type of data is indicated by the shaded bars, which indicate an average patient health score 614 is determined prior to the wrist procedure (e.g., pre-op), 6-months removed from the wrist procedure (e.g., 0-6 mos.), 12 months removed from the wrist procedure (e.g., 6-12 mos.), 2 years removed from the wrist procedure (e.g., 1-2 y.), and 2 or more years removed from the wrist procedure (e.g., 2y+). Accordingly, the shaded bar graphs provided an indication of average patient health scores prior to receiving the wrist procedure and at multiple points in time after have received the wrist procedure.

In addition, the mobile application may provide a second type of output data. For example, the mobile application also provides an indication regarding the number of patients in each respective time period who fell within the age of 45-87 as of the date of treatment. The age range may be customizable using the age toggles 617, 618. The first age toggle 617 may be slid in order to adjust the lower end of the age range. The second age toggle 618 may be slid in order to adjust the upper end of the age range. Such age data may be retrieved from an implementation of a medical instrument index that stores patient ages that have been extracted from medical study instruments.

Figure 7:
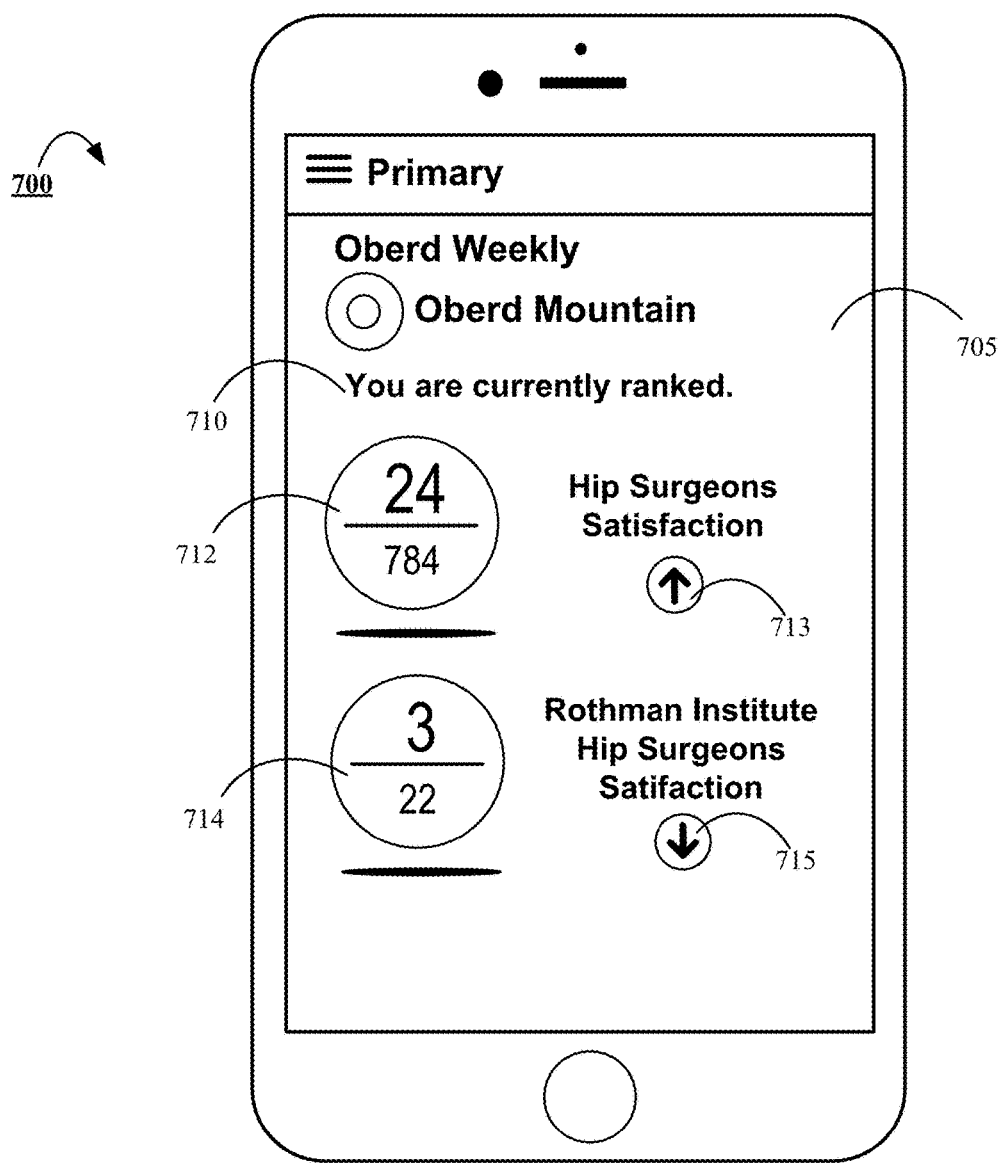
FIG. 7 is a depiction of an example of a graphical user interface for displaying a report that includes data derived from search results identified using a medical instrument index.

FIG. 7 is a depiction of an example of a graphical user interface 705 for displaying a report that includes data derived from search results identified using a medical instrument index.

The medical study instrument index may be searched to identify data that can be analyze to evaluate providers. For instance, a representative patient pre-score and representative patient post-procedure score can be used to evaluate providers who have achieved the greatest increase in patient health scores after providing a particular procedure. In such instances, providers can be ranked, based the level of increase that their patients have achieved. Such rankings can be performed for all providers nationwide, worldwide, or the like may be determined and reported periodically (e.g., once a week, once a month, once a year, or the like). Alternatively, such rankings can be determined and reported in response to a user request.

The user device 700 provides a graphical user interface 705 that displays a report that was generated showing a particular provider's rankings. For instance, the report indicates to the user of the user device 700 that the provider is ranked. In this particular example, the provider was determined to be ranked 24th out of 784 hip surgeons 712. The graphical icon 714 indicates that the doctor's performance has increased. Separately, the report also indicates to the user of the user device that the provider was determined to be 3rd out of 22 hip surgeons at the Rothman Institute. The graphical icon 715 indicates to the user of the user device that the provider's rank has decreased since the last report.

Embodiments of the subject matter, the functional operations and the processes described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

What is claimed is:

1. A method comprising:
   receiving, by the search engine, a search query that identifies particular procedure criteria from a user device;
   in response to receiving, by the search engine, the search query that identifies the particular procedure criteria, accessing, by the search engine, a medical study instrument index that includes a plurality of index entries,
      wherein the medical study instrument index is a data structure that is separate from the medical study instruments that are indexed by the medical study instrument index, wherein each index entry of the medical study instrument index includes a plurality of fields structuring index data,
      wherein each respective index entry of the plurality of index entries (i) represents data that has been extracted from a respective medical study instrument and (ii) references a patient health score of the respective medical study instrument upon which the respective index entry is based, wherein the plurality of index entries are collectively organized based on procedure type;
   determining, by the search engine using one or more of the plurality of index entries in the medical study instrument index, a first patient health score that is representative of biometric data that is independent of a procedure specified by the particular procedure criteria identified in the search query;
   determining, by the search engine using one or more index entries in the medical study instrument index, a second patient health score that is representative of biometric data that is dependent on a procedure specified by the particular procedure criteria identified in the search query; and
   generating, by the search engine, a page for display on the user device that includes a first graphical element representing the first patient health score and a second graphical element representing the second patient health score, wherein generating, by the search engine, the page for display on the user device comprises:
      generating a table that includes a first row and a second row, wherein the first row includes a numerical representation of a value associated with the first patient health score and the second row provides numerical representation of a value associated with the second patient health score.

2. The method of claim 1, the method further comprising:
   maintaining, by a search engine, a medical study instrument index that organizes data based on procedure type, wherein each index entry in the medical study instrument index includes a procedure type includes:
      obtaining one or more populated medical study instruments;
      for each particular medical study instrument of the one or more obtained medical study instruments:
         extracting treatment data from one or more fields of the particular medical study instrument, wherein the extracted treatment data includes a procedure type;
         generating an index entry for the particular medical study instrument that includes the procedure type; and
         storing the generated index entry in the medical study instrument index.

3. The method of claim 1, wherein accessing, by the search engine, the medical study instrument index that is organized based on procedure type comprises:
identifying, by the search engine, a set of index entries that include a procedure type that satisfies the procedure criteria identified in the search query.

4. The method of claim 1, wherein the first patient health score that is representative of biometric data that is independent of the procedure specified by the particular procedure criteria identified in the search query includes an average of multiple scores that each indicate the state of an entity prior to the entity receiving the procedure specified by the particular procedure criteria identified in the search query.

5. The method of claim 1, the second patient health score that is representative of biometric data that is dependent on a procedure specified by the particular procedure criteria identified in the search query includes an average of multiple scores that each indicate the state of an entity after the entity has received the procedure specified by the particular procedure criteria identified in the search query.

6. The method of claim 1, wherein generating, by the search engine, a page for display on the user device that includes a first graphical element representing the first patient health score and a second graphical element representing the second patient health score comprises:
generating a bar graph that includes a first bar and a second bar, wherein the first bar provides a graphical representation of a value associated with the first patient health score and the second bar provides a graphical representation of a value associated with the second patient health score.

7. A system comprising:
one or more computers and one or more storage devices storing instructions that are operable, when executed by one or more computers, to cause the one or more computers to perform operations comprising:
receiving, by the search engine, a search query that identifies particular procedure criteria from a user device;
in response to receiving, by the search engine, the search query that identifies the particular procedure criteria, accessing, by the search engine, a medical study instrument index that includes a plurality of index entries,
wherein the medical study instrument index is a data structure that is separate from the medical study instruments that are indexed by the medical study instrument index, wherein each index entry of the medical study instrument index includes a plurality of fields structuring index data,
wherein each respective index entry of the plurality of index entries (i) represents data that has been extracted from a respective medical study instrument and (ii) references a patient health score of the respective medical study instrument upon which the respective index entry is based, wherein the plurality of index entries are collectively organized based on procedure type;
determining, by the search engine using one or more of the plurality of index entries in the medical study instrument index, a first patient health score that is representative of biometric data that is independent of a procedure specified by the particular procedure criteria identified in the search query;
determining, by the search engine using one or more index entries in the medical study instrument index, a second patient health score that is representative of biometric data that is dependent on a procedure specified by the particular procedure criteria identified in the search query; and
generating, by the search engine, a page for display on the user device that includes a first graphical element representing the first patient health score and a second graphical element representing the second patient health score, wherein generating, by the search engine, the page for display on the user device comprises:
generating a table that includes a first row and a second row, wherein the first row includes a numerical representation of a value associated with the first patient health score and the second row provides numerical representation of a value associated with the second patient health score.

8. The system of claim 7, the operations further comprising:
maintaining, by a search engine, a medical study instrument index that organizes data based on procedure type, wherein each index entry in the medical study instrument index includes a procedure type includes:
obtaining one or more populated medical study instruments;
for each particular medical study instrument of the one or more obtained medical study instruments:
extracting treatment data from one or more fields of the particular medical study instrument, wherein the extracted treatment data includes a procedure type;
generating an index entry for the particular medical study instrument that includes the procedure type; and
storing the generated index entry in the medical study instrument index.

9. The system of claim 7,
wherein the first patient health score that is representative of biometric data that is independent of the procedure specified by the particular procedure criteria identified in the search query includes an average of multiple scores that each indicate the state of an entity prior to the entity receiving the procedure specified by the particular procedure criteria identified in the search query.

10. The system of claim 7,
the second patient health score that is representative of biometric data that is dependent on a procedure specified by the particular procedure criteria identified in the search query includes an average of multiple scores that each indicate the state of an entity after the entity has received the procedure specified by the particular procedure criteria identified in the search query.

11. The system of claim 7, wherein generating, by the search engine, a page for display on the user device that includes a first graphical element representing the first patient health score and a second graphical element representing the second patient health score comprises:
generating a bar graph that includes a first bar and a second bar, wherein the first bar provides a graphical representation of a value associated with the first patient health score and the second bar provides a graphical representation of a value associated with the second patient health score.

12. The system of claim 7, wherein generating, by the search engine, a page for display on the user device that includes a first graphical element representing the first patient health score and a second graphical element representing the second patient health score comprises:

generating a table that includes a first row and a second row, wherein the first row includes a numerical representation of a value associated with the first output and the second row provides numerical representation of a value associated with the second output.

13. A non-transitory computer-readable medium storing software comprising instructions executable by one or more computers which, upon such execution, cause the one or more computers to perform operations comprising:
receiving, by the search engine, a search query that identifies particular procedure criteria from a user device;
in response to receiving, by the search engine, the search query that identifies the particular procedure criteria, accessing, by the search engine, a medical study instrument index that includes a plurality of index entries, wherein the medical study instrument index is a data structure that is separate from the medical study instruments that are indexed by the medical study instrument index, wherein each index entry of the medical study instrument index includes a plurality of fields structuring index data,
wherein each respective index entry of the plurality of index entries (i) represents data that has been extracted from a respective medical study instrument and (ii) references a patient health score of the respective medical study instrument upon which the respective index entry is based, wherein the plurality of index entries are collectively organized based on procedure type;
determining, by the search engine using one or more of the plurality of index entries in the medical study instrument index, a first patient health score that is representative of biometric data that is independent of a procedure specified by the particular procedure criteria identified in the search query;
determining, by the search engine using one or more index entries in the medical study instrument index, a second patient health score that is representative of biometric data that is dependent on a procedure specified by the particular procedure criteria identified in the search query; and
generating, by the search engine, a page for display on the user device that includes a first graphical element representing the first patient health score and a second graphical element representing the second patient health score, wherein generating, by the search engine, the page for display on the user device comprises:
generating a table that includes a first row and a second row, wherein the first row includes a numerical representation of a value associated with the first patient health score and the second row provides numerical representation of a value associated with the second patient health score.

14. The computer-readable medium of claim 13, the operations further comprising:
maintaining, by a search engine, a medical study instrument index that organizes data in a medical study instrument database based on procedure type, wherein each index entry in the medical study instrument index includes a procedure type includes:

obtaining one or more populated medical study instruments;
for each particular medical study instrument of the one or more obtained medical study instruments:
extracting treatment data from one or more fields of the particular medical study instrument, wherein the extracted treatment data includes a procedure type;
generating an index entry for the particular medical study instrument that includes the procedure type; and
storing the generated index entry in the medical study instrument index.

15. The computer-readable medium of claim 13, wherein accessing, by the search engine, the medical study instrument index that is organized based on procedure type comprises:
identifying, by the search engine, a set of index entries that include a procedure type that satisfies the procedure criteria identified in the search query.

16. The computer-readable medium of claim 13,
the first patient health score that is representative of biometric data that is independent of the procedure specified by the particular procedure criteria identified in the search query includes an average of multiple scores that each indicate the state of an entity prior to the entity receiving the procedure specified by the particular procedure criteria identified in the search query.

17. The computer-readable medium of claim 13,
the second patient health score that is representative of biometric data that is dependent on a procedure specified by the particular procedure criteria identified in the search query includes an average of multiple scores that each indicate the state of an entity after the entity has received the procedure specified by the particular procedure criteria identified in the search query.

18. The computer-readable medium of claim 13, wherein generating, by the search engine, a page for display on the user device that includes a first graphical element representing the first patient health score and a second graphical element representing the second patient health score comprises:
generating a bar graph that includes a first bar and a second bar, wherein the first bar provides a graphical representation of a value associated with the first patient health score and the second bar provides a graphical representation of a value associated with the second patient health score.

19. The computer-readable medium of claim 13, wherein generating, by the search engine, a page for display on the user device that includes a first graphical element representing the first patient health score and a second graphical element representing the second patient health score comprises:
generating a table that includes a first row and a second row, wherein the first row includes a numerical representation of a value associated with the first patient health score and the second row provides numerical representation of a value associated with the second patient health score.

* * * * *